US009629609B2

(12) United States Patent
Matsumoto et al.

(10) Patent No.: US 9,629,609 B2
(45) Date of Patent: *Apr. 25, 2017

(54) ULTRASOUND ELEMENT AND ULTRASOUND ENDOSCOPE (71) Applicants: OLYMPUS MEDICAL SYSTEMS CORP., Tokyo (JP); OLYMPUS CORPORATION, Tokyo (JP)

(72) Inventors: Kazuya Matsumoto, Nagano (JP); Kazuhisa Karaki, Shiojiri (JP); Mamoru Hasegawa, Nagano (JP); Katsuhiro Wakabayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 683 days.

This patent is subject to a terminal disclaimer.

(21) Appl. No.: 14/150,210

(22) Filed: Jan. 8, 2014

(65) Prior Publication Data

US 2014/0121526 A1    May 1, 2014

Related U.S. Application Data (63) Continuation of application No. PCT/JP2012/063792, filed on May 29, 2012.

(30) Foreign Application Priority Data

Jul. 11, 2011  (JP) .................................. 2011-153278

(51) Int. Cl.
*A61B 8/00* (2006.01)
*A61B 8/12* (2006.01)
(Continued)

(52) U.S. Cl.
CPC .............. *A61B 8/4483* (2013.01); *A61B 8/12* (2013.01); *A61B 8/445* (2013.01); *B06B 1/0292* (2013.01);
(Continued)

(58) Field of Classification Search
CPC .... A61B 8/14; A61B 8/12; A61B 8/00; G01B 17/06
See application file for complete search history.

(56) References Cited

U.S. PATENT DOCUMENTS

| 8,047,995 | B2 | 11/2011 | Wakabayashi et al. |
| 2003/0006481 | A1 | 1/2003 | Miyada et al. |
| 2014/0128741 | A1* | 5/2014 | Matsumoto ............. A61B 8/12 600/463 |

FOREIGN PATENT DOCUMENTS

| EP | 1 911 529 A1 | 10/2007 |
| EP | 2 030 698 A1 | 3/2009 |

(Continued)

OTHER PUBLICATIONS

Extended Supplementary European Search Report dated Mar. 9, 2015 from related European Application No. 12 81 1284.4.

(Continued)

*Primary Examiner* — Joel Lamprecht
(74) *Attorney, Agent, or Firm* — Scully, Scott, Murphy & Presser, P.C.

(57) ABSTRACT

A US element includes a silicon substrate, wherein a lower electrode layer that has a plurality of lower electrode sections, and a plurality of lower wiring sections, and is connected to a lower electrode terminal to which a drive signal and a bias signal are applied, a lower insulating layer, an upper insulating layer in which a plurality of cavities are formed, an upper electrode layer that has a plurality of upper electrode sections and a plurality of upper wiring sections, and is connected to an upper electrode terminal at a ground potential for detecting a capacitance signal, and a protection layer are sequentially stacked on the silicon substrate, and the US element further includes a shield electrode section (Continued)

that is formed at least at an upper side of the lower wiring sections, and is connected to a shield electrode terminal at a ground potential.

8 Claims, 11 Drawing Sheets

(51) Int. Cl.
     *H02N 1/00*           (2006.01)
     *H02N 1/08*           (2006.01)
     *B06B 1/02*           (2006.01)

(52) U.S. Cl.
     CPC ............... *H02N 1/002* (2013.01); *H02N 1/08* (2013.01); *B06B 2201/76* (2013.01)

(56) References Cited

FOREIGN PATENT DOCUMENTS

| | | |
|---|---|---|
| JP | 2009-050560 A | 3/2009 |
| JP | 2009-055474 A | 3/2009 |

OTHER PUBLICATIONS

International Search Report dated Jul. 10, 2012 issued in PCT/JP2012/063792.

\* cited by examiner

ULTRASOUND ELEMENT AND ULTRASOUND ENDOSCOPE

CROSS REFERENCE TO RELATED APPLICATION

This application is a continuation application of PCT/JP2012/063792 filed on May 29, 2012 and claims benefit of Japanese Application No. 2011-153278 filed in Japan on Jul. 11, 2011, the entire contents of which are incorporated herein by this reference.

BACKGROUND OF THE INVENTION

1. Field of the Invention

The present invention relates to an electrostatic capacitance type ultrasound element, and an ultrasound endoscope including the ultrasound element.

2. Description of the Related Art

An ultrasound diagnostic method by which an inside of a body is irradiated with ultrasound to image a state of the inside of the body from an echo signal for diagnosis comes into widespread use. One of the ultrasound diagnostic apparatuses for use in the ultrasound diagnostic method is an ultrasound endoscope (hereinafter called a "US endoscope"). In a US endoscope, an ultrasound transducer is placed at a distal end rigid portion of an insertion portion that is introduced into a body. An ultrasound transducer has a function of converting an electric signal into ultrasound, transmitting the ultrasound into a body, and receiving the ultrasound reflected at the inside of the body to convert the ultrasound into an electric signal.

So far, for ultrasound transducers, ceramics piezoelectric materials containing lead having a large environmental load, for example, PZT (lead zirconate titanate) has been mainly used. In contrast with this, Caronti et al. discloses an electrostatic capacitance ultrasound transducer (capacitive micromachined ultrasonic transducer; hereinafter called a "c-MUT") that is produced with use of a MEMS (micro electro mechanical systems) technique, and does not contain lead in the material. A c-MUT has an ultrasound cell (hereinafter, called a "US cell") in which an upper electrode section and a lower electrode section are disposed to face each other via a void portion (cavity), as a unit element. A plurality of US cells with respective electrode sections connected by wiring sections are arranged, and an ultrasound element (hereinafter, called a "US element") is configured.

The US cell vibrates a membrane (a vibration portion) including the upper electrode section by an electrostatic force by applying a voltage to between the lower electrode section and the upper electrode section, and generates ultrasound. When ultrasound enters from an outside, a space between both the electrodes changes, and therefore, the ultrasound is converted into an electric signal from a change of an electrostatic capacitance. Note that not only at the time of ultrasound reception and transmission, but also at the time of ultrasound reception, a predetermined bias voltage is applied to between the electrodes in order to enhance efficiency of transmission and reception.

In a c-MUT, in order to obtain stable characteristics, a drive signal for generating ultrasound and a bias signal for receiving ultrasound are applied to the lower electrode section, and the upper electrode section is always at a ground potential (grounding potential).

SUMMARY OF THE INVENTION

An ultrasound element of an embodiment of the present invention includes a base substrate, wherein a lower electrode layer that has a plurality of lower electrode sections, and a plurality of lower wiring sections that connect the plurality of lower electrode sections, and is connected to a lower electrode terminal to which a drive signal and a bias signal are applied, a lower insulating layer, an upper insulating layer in which a plurality of cavities are formed, an upper electrode layer that has a plurality of upper electrode sections that are disposed to face the respective lower electrode sections via the respective cavities, and a plurality of upper wiring sections that connect the plurality of upper electrode sections, and is connected to an upper electrode terminal at a ground potential, for detecting a capacitance signal, and a protection layer are sequentially stacked on the base substrate, and further includes a shield electrode section that is formed at least at an upper side of the lower wiring sections, and is connected to a shield electrode terminal at a ground potential.

Further, an ultrasound endoscope of another embodiment of the present invention has an ultrasound element including a base substrate, wherein a lower electrode layer that has a plurality of lower electrode sections, and a plurality of lower wiring sections that connect the plurality of lower electrode sections, and is connected to a lower electrode terminal to which a drive signal and a bias signal are applied, a lower insulating layer, an upper insulating layer in which a plurality of cavities are formed, an upper electrode layer that has a plurality of upper electrode sections that are disposed to face the respective lower electrode sections via the respective cavities, and a plurality of upper wiring sections that connect the plurality of upper electrode sections, and is connected to an upper electrode terminal at a ground potential, for detecting a capacitance signal, and a protection layer are sequentially stacked on the base substrate, and further including a shield electrode section that is formed at least at an upper side of the lower wiring sections, and is connected to a shield electrode terminal at a ground potential.

DETAILED DESCRIPTION OF THE PREFERRED EMBODIMENTS

First Embodiment

Hereinafter, an ultrasound element 20 of a first embodiment, and an ultrasound endoscope 2 having the ultrasound element 20 will be described with reference to the drawings.
<Configuration of Ultrasound Endoscope>

Figure 1:
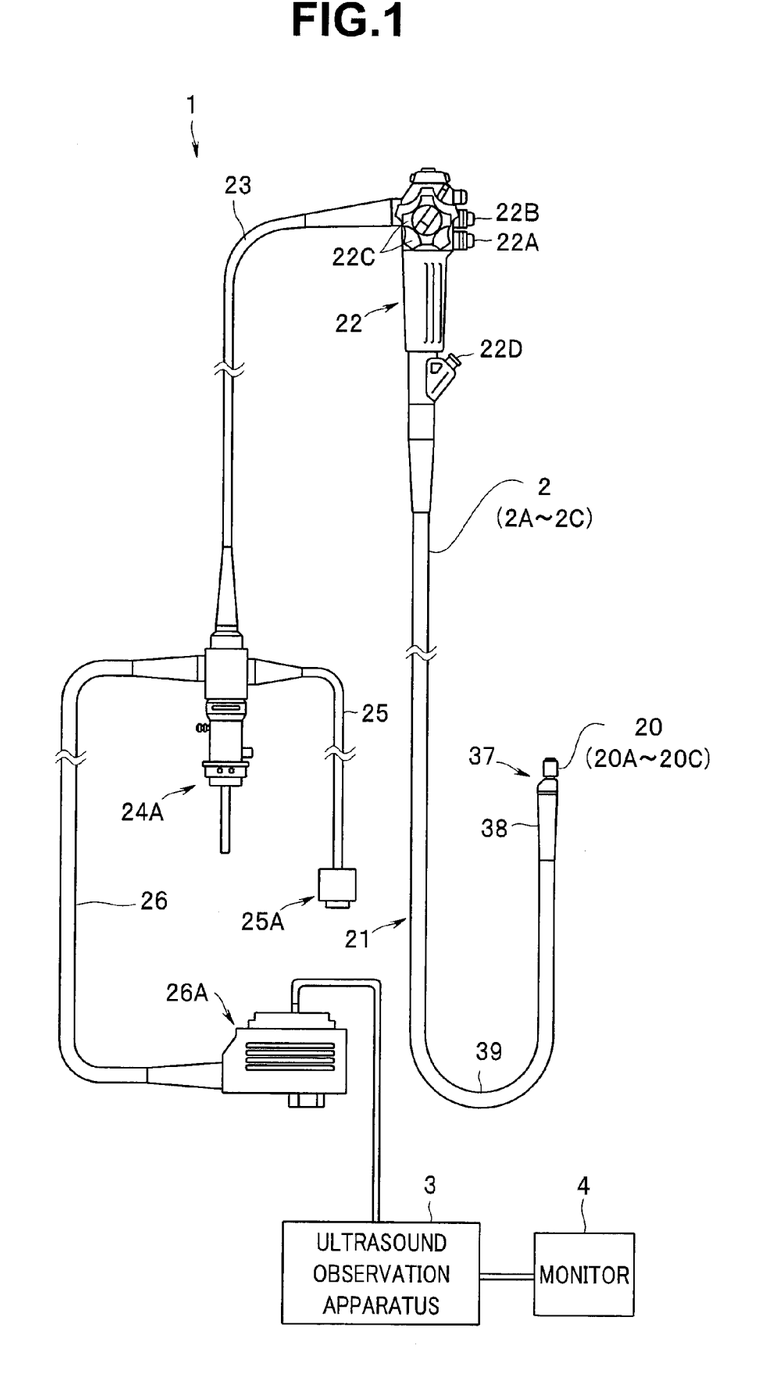
FIG. 1 is an external view for explaining an ultrasound endoscope of a first embodiment.

As shown in FIG. 1, a US endoscope 2 configures an ultrasound endoscope system 1 with an ultrasound observation apparatus 3 and a monitor 4. The US endoscope 2 includes an elongated insertion portion 21 that is inserted into a body, an operation portion 22 that is placed at a proximal end of the insertion portion 21, and a universal cord 23 that is extended from a side portion of the operation portion 22.

At a proximal end portion of the universal cord 23, a connector 24A that is connected to a light source apparatus (not illustrated) is placed. From the connector 24A, a cable 25 that is detachably connected to a camera control unit (not illustrated) via a connector 25A, and a cable 26 that is detachably connected to the ultrasound observation apparatus 3 via a connector 26A are extended. The monitor 4 is connected to the ultrasound observation apparatus 3.

The insertion portion 21 is configured by being connectively provided with a distal end rigid portion (hereinafter, called a "distal end portion") 37, a bending portion 38 that is located at a rear end of the distal end portion 37, and a flexible tube portion 39 that is located at a rear end of the bending portion 38 to reach the operation portion 22, has a small diameter, a long length and flexibility, in sequence from a distal end side. At a distal end side of the distal end portion 37, an ultrasound unit 30 is placed.

In the operation portion 22, an angle knob 22A that performs bending control of the bending portion 38 to a desired direction, an air feeding/water feeding button 22B that performs an air feeding and a water feeding operations, a suction button 22C that performs a suction operation, a treatment instrument insertion port 22D that is an inlet port for a treatment instrument that is introduced into a body and the like are placed.

Figure 2:
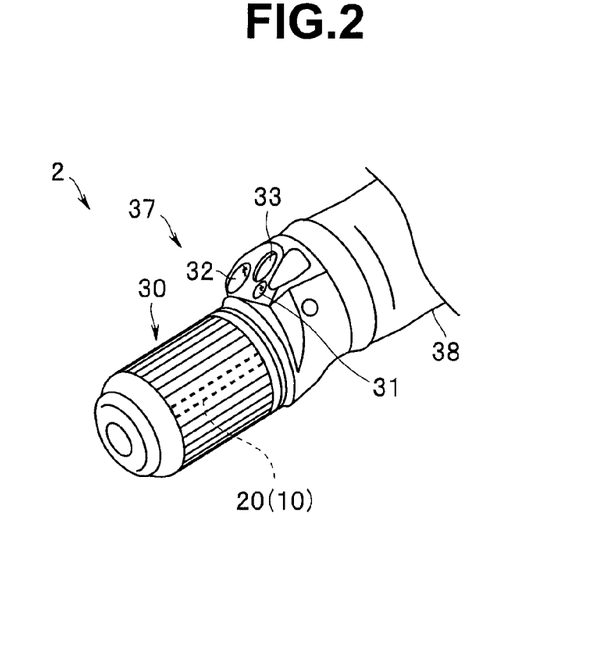
FIG. 2 is a perspective view for explaining a distal end portion of the ultrasound endoscope of the first embodiment.

As shown in FIG. 2, in the distal end portion 37 in which the ultrasound unit (US unit) 30 is provided, an illumination lens cover 31 that configures an illumination optical system, an observation lens cover 32 of an observation optical system, a forceps port 33 that is also used as a suction port, and an air feeding/water feeding nozzle not illustrated are placed.

Figure 3:
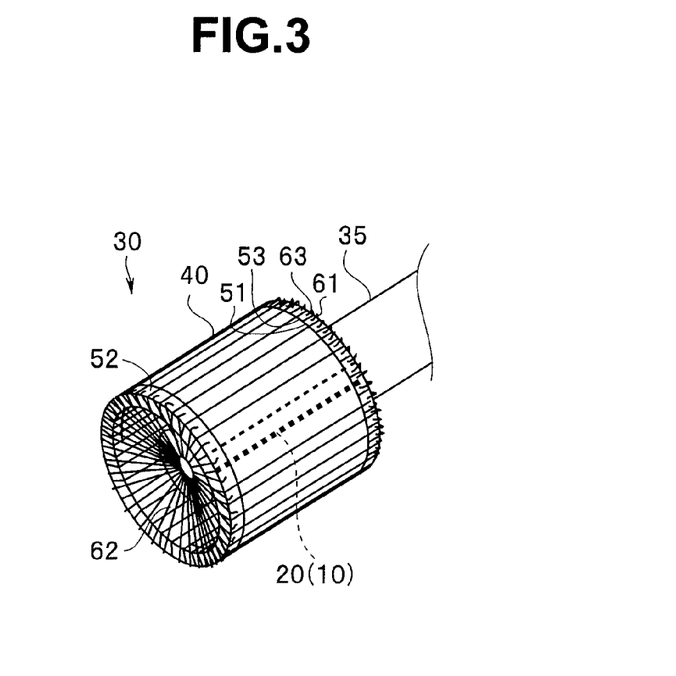
FIG. 3 is a perspective view for explaining a configuration of an ultrasound array at the distal end portion of the ultrasound endoscope of the first embodiment.

As shown in FIG. 3, an ultrasound array (US array) 40 of the US unit 30 is a radial type transducer group in which long sides of a plurality of ultrasound elements 20 rectangular in plain view are connected and roundly disposed in a cylinder shape. Namely, in the US array 40, 200 of US elements 20 each with a short side of 0.1 mm or less are placed in a direction of 360 degrees on a side surface of a cylinder with a diameter of 2 mm, for example. Note that the US array 40 is a radial type transducer group, but the US array may be a convex type transducer group that is folded into a convex shape.

At an end portion of the ultrasound array 40 in a cylindrical shape, a plurality of lower electrode terminals 52 are arranged, and are respectively connected to respective signal lines 62 of a coaxial cable bundle 35. The upper electrode terminals 51 are respectively connected to respective capacitance detection lines 61 of the coaxial cable bundle 35. Shield electrode terminals 53 are respectively connected to shielding wires 63 of the coaxial cable bundle 35. Namely, the coaxial cable bundle 35 includes coaxial cables having the same number of core wires as a total number of a plurality of signal lines 62 and a plurality of capacitance detection lines 61.

The coaxial cable bundle 35 is inserted through the distal end portion 37, the bending portion 38, the flexible tube portion 39, the operation portion 22, the universal cord 23 and the ultrasound cable 26, and is connected to the ultrasound observation apparatus 3 via the ultrasound connector 26A.
<Configuration of Transmission and Reception Section>

Next, with use of FIG. 4, FIG. 5 and FIG. 6, configurations of the US element 20 and an ultrasound cell (US cell) 10 will be described. Note that the drawings are all schematic views for explanation, and the number, thicknesses, sizes and the ratios of the sizes and the like of the patterns differ from reality.

Figure 4:
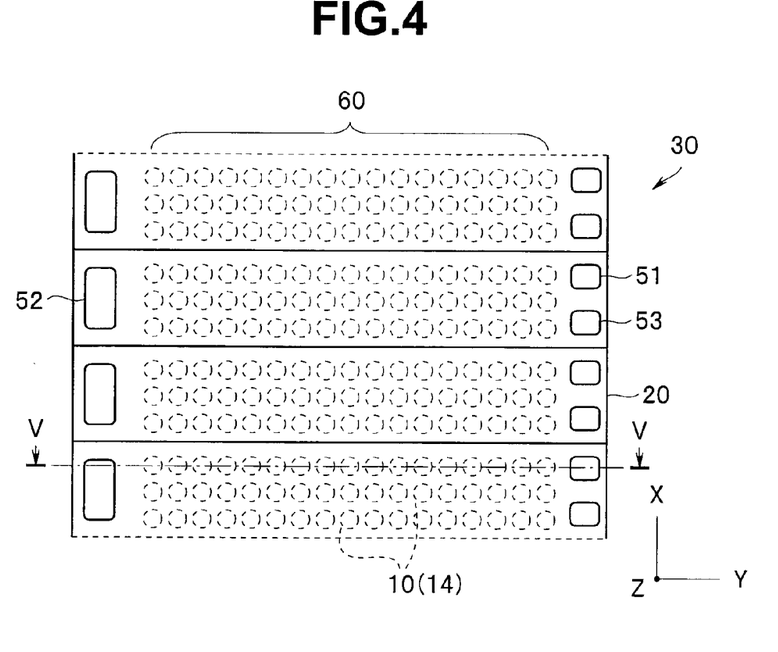
FIG. 4 is a top view for explaining a structure of an ultrasound element of the first embodiment.

As shown in FIG. 4, in the US elements 20, a plurality of electrostatic capacitance type US cells 10 are disposed in a matrix shape. Note that for explanation, only some of the US cells 10 are shown in FIG. 4. Disposition of the US cells 10 may be regular grid disposition, staggered disposition, triangular mesh disposition or the like, or may be random disposition. At one end portion of the US element 20, the lower electrode terminal 52 is placed, and at the other end portion, the upper electrode terminal 51 and the shield electrode terminal 53 are placed.

Figure 5:
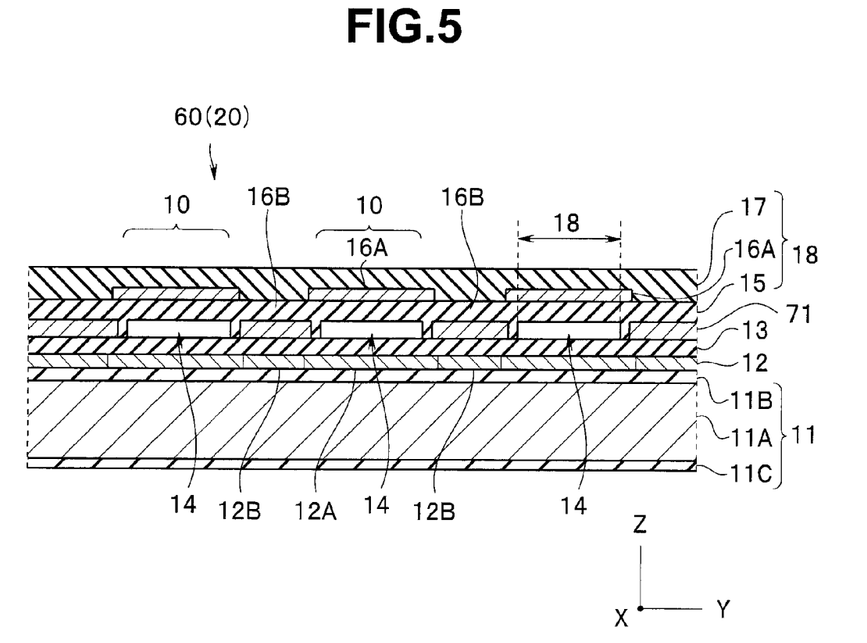
FIG. 5 is a partial sectional view taken along the V-V line of FIG. 4, for explaining the structure of the ultrasound element of the first embodiment.
Figure 6:
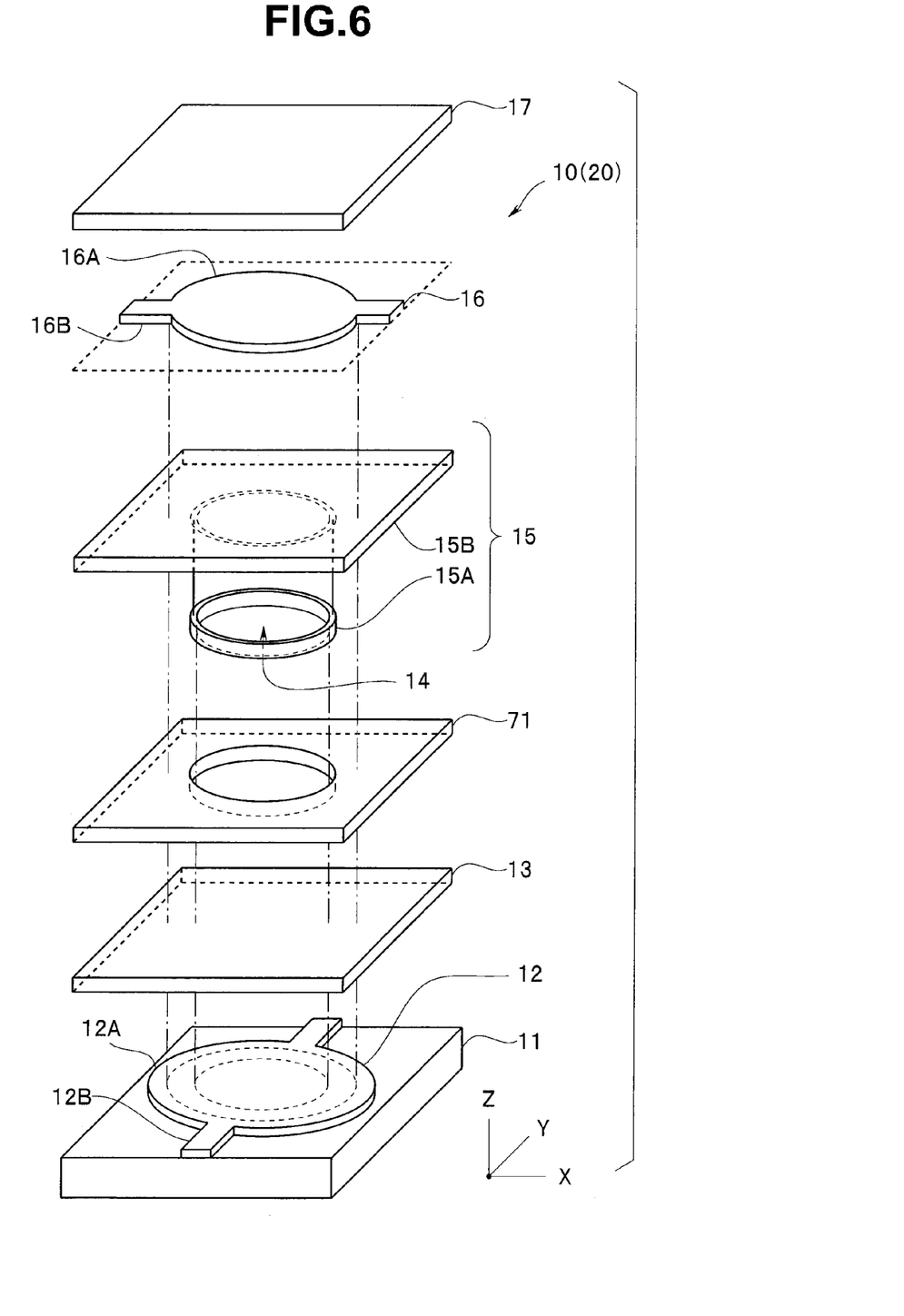
FIG. 6 is an exploded view for explaining a structure of an ultrasound cell of the first embodiment.

As shown in FIG. 5 and FIG. 6, a US cell 10 has, on a silicon substrate 11 that is a base substrate, a lower electrode layer 12 that is connected to the lower electrode terminal 52, a lower insulating layer (a first insulating layer) 13, an upper insulating layer (a second insulating layer) 15 in which cavities 14 in a cylindrical shape are formed, an upper electrode layer 16 that is connected to the upper electrode terminal 51, and a protection layer (a third insulating layer) 17, which are stacked in sequence. The silicon substrate 11 is a substrate in which silicon thermal oxide films 11B and 11C are formed on a surface of a silicon 11A.

Namely, the respective US cells 10 each have a lower electrode section 12A and an upper electrode section 16A that are disposed to face each other via the cavity 14.

The lower electrode layer 12 has a plurality of lower electrode sections 12A that are circular in plain view, and a plurality of lower wiring sections 12B that are provided extensively in two directions from edge side portions of the lower electrode sections 12A. The lower wiring sections 12B connect the lower electrode sections 12A of another US cell of the same US element 20. The lower wiring section 12B is connected to the lower electrode terminal 52.

The upper electrode layer 16 has a plurality of upper electrode sections 16A that are circular in plain view, and a plurality of upper wiring sections 16B that are provided extensively in two directions from edge side portions of the upper electrode sections 16A. The upper wiring sections 16B connect the upper electrode sections 16A of other US cells of the same US element 20. The upper wiring sections 16B are connected to the upper electrode terminals 51.

Namely, all the lower electrode sections 12A of a plurality of US cells 10 that are disposed in the same US element 20 are connected to one another, and all the upper electrode sections 16A are also connected to one another.

In the US cell 10 of the above described structure shown in FIG. 5 and FIG. 6, the upper insulating layer 15, the upper electrode layer 16 and the protection layer 17 in a region directly above the cavity 14 configure a membrane 18 that is a vibration section.

The US cell 10 has a shield electrode section 71 on an outer circumferential portion of the cavity 14. The shield electrode section 71 is an electrode that is formed on a region including an upper side of the lower wiring section 12B and is formed of a conductive material, and is connected to the shield electrode terminal 53. As will be described later, the cavity 14 is a region where a sacrificial layer 70 that is covered with the upper insulating layer 15 and is formed of a conductive material is partially removed by an etching process, and the shield electrode section 71 is a remaining region of the sacrificial layer 70 that is not removed by the etching process.

Note that in FIG. 6, for the sake of illustration, the upper insulating layer 15 is shown by being divided into an upper insulating layer 15A and an upper insulating layer 15B, but the upper insulating layer 15A and the upper insulating layer 15B are integrally formed simultaneously. A portion that enters a groove section 70A that is formed in the sacrificial layer 70 is the upper insulating layer 15A.

In the US element 20, an upper side of the lower wiring section 12B is covered with not only the lower insulating layer 13, the upper insulating layer 15 and the protection layer 17, but also the shield electrode section 71. The shield electrode section 71 is always at a ground potential via the shield electrode terminal 53.

Therefore, even if a part of the insulating film is broken due to dust, a defect or the like, the voltage signals (the drive signal and the bias signal) that are applied to the lower electrode layer 12 do not leak to the outside of the US cell 10. Therefore, characteristics of the US cell 10 and the US endoscope 2 are stable.

Further, since the shield electrode section 71 is produced with use of the sacrificial layer 70, increase in the number of steps is small, and manufacture thereof is easy.

<Manufacturing Method of US Element>

Next, with use of FIG. 7A to FIG. 7F, FIG. 8 and FIG. 9, a manufacturing method of the US element 20 will be briefly described.

<Step S11> Formation of the Lower Electrode Layer

A conductive material made of conductive silicon or a metal, for example, copper, gold or aluminum is deposited on an entire surface of the silicon substrate 11 by a sputtering method or the like. Subsequently, a mask pattern is formed by photolithography, and thereafter, is partially removed by etching, whereby the lower electrode layer 12 that has the lower electrode section 12A and the lower wiring section 12B is formed.

<Step S12> Formation of the Lower Insulating Layer

The lower insulating layer 13 formed of an insulating material such as SiN is deposited by, for example, a CVD method (a chemical vapor deposition method) in such a manner as to cover the lower electrode layer 12.

<Step S13> Formation of the Sacrificial Layer

Figure 7A:
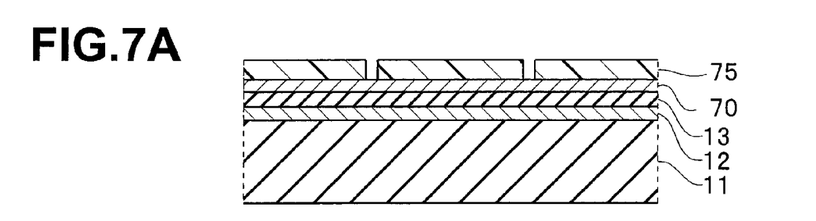
FIG. 7A is a sectional view for explaining a manufacturing method of the ultrasound cell of the first embodiment.

On the lower insulating layer 13, a sacrificial layer material formed of a material that is selected from conductive materials and is removable by etching is deposited. Subsequently, a mask pattern 75 by photolithography is formed on the sacrificial layer 70 as shown in FIG. 7A.

<Step S14> Sacrificial Layer Patterning

Figure 7B:
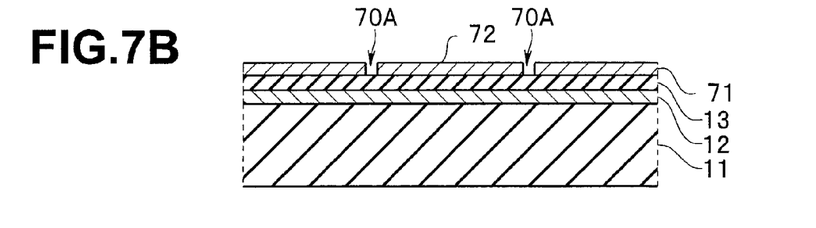
FIG. 7B is a sectional view for explaining the manufacturing method of the ultrasound cell of the first embodiment.
Figure 8:
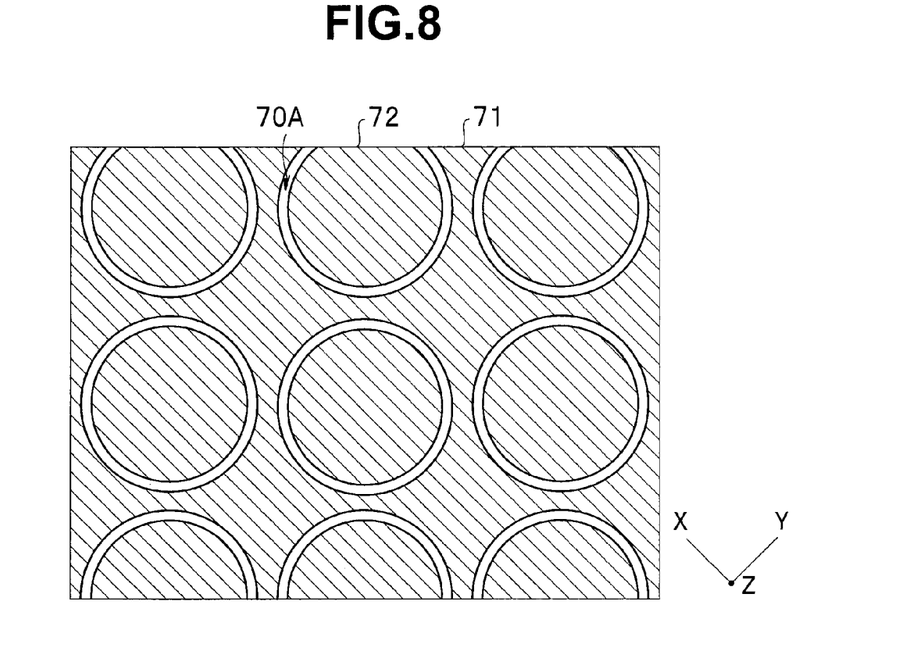
FIG. 8 is a top view showing a pattern of a sacrificial layer of the ultrasound cell of the first embodiment.

As shown in FIG. 7B and FIG. 8, the sacrificial layer 70 is divided into a cavity section 72 in a shape of a cavity (columnar shape) and the shield electrode section 71 via a doughnut-shaped groove section 70A by an etching process.

Since a thickness of the sacrificial layer 70 corresponds to a height of the cavity 14, and therefore, is, for example, 0.05 to 0.3 μm, and is preferably 0.05 to 0.15 μm.

<Step S15> Formation of the Upper Insulating Layer

Figure 7C:
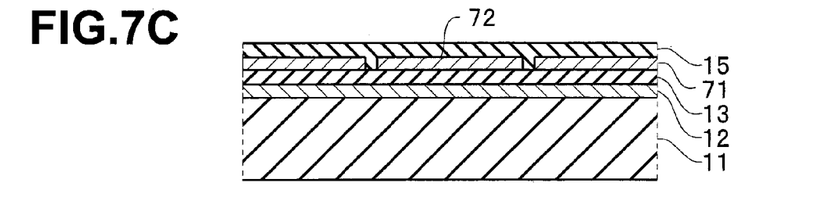
FIG. 7C is a sectional view for explaining the manufacturing method of the ultrasound cell of the first embodiment.

As shown in FIG. 7C, on a top surface of the sacrificial layer pattern (the cavity section 72 and the shield electrode section 71), the upper insulating layer 15 is formed by the method and the material similar to those for the lower insulating layer 13, for example. At this time, the upper insulating layer 15A is also formed in an inside of the groove section 70A, as already described.

Subsequently, in a predetermined position of the upper insulating layer 15, an opening portion (not illustrated) in which an etching agent is poured is formed in order to remove the cavity section 72.

<Step S16> Formation of the Cavity

Figure 7D:
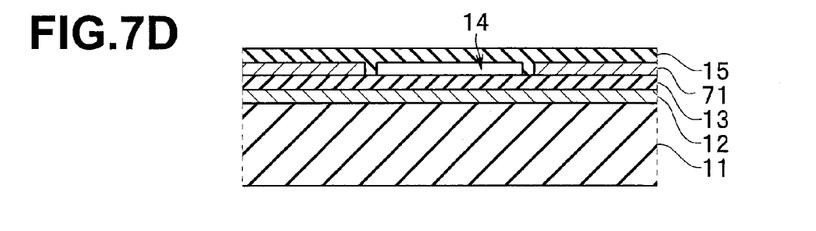
FIG. 7D is a sectional view for explaining the manufacturing method of the ultrasound cell of the first embodiment.
Figure 9:
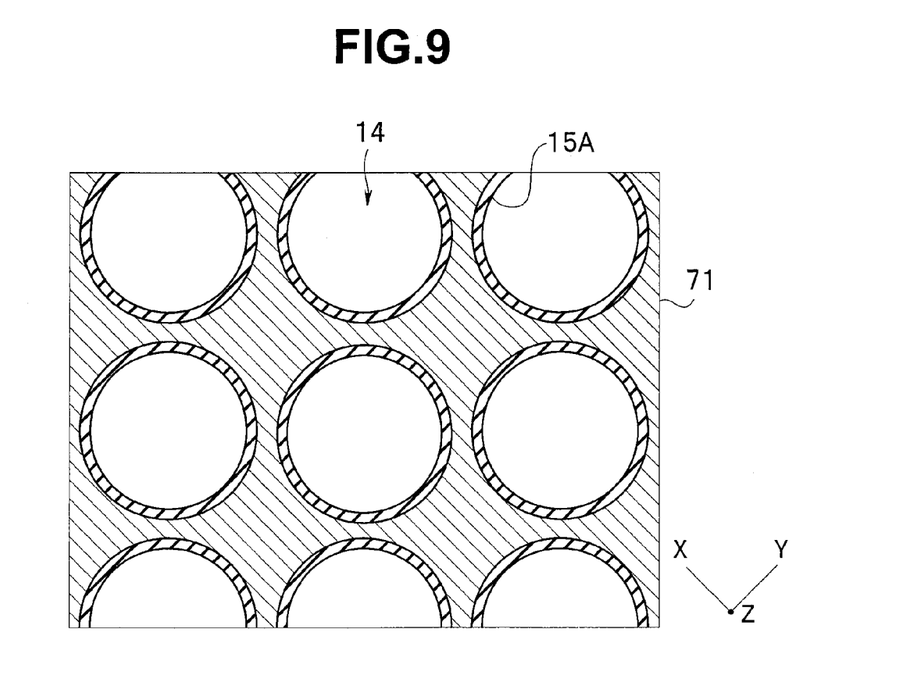
FIG. 9 is a top view showing a pattern of a shield electrode section of the ultrasound cell of the first embodiment.

Next, as shown in FIG. 7D and FIG. 9, the cavity 14 is formed by removal of the cavity section 72 by etching. The shield electrode section 71 is separated from the cavity section 72 by the upper insulating layer 15A, and therefore, is not removed by the etching agent. Namely, the shield electrode section 71 is the remaining region of the sacrificial layer 70 that is not removed by the etching process.

For example, when tungsten (W) is used as the sacrificial layer 70, and silicon nitride (SiN) is used as the lower insulating layer 13 and the upper insulating layer 15, a hydrogen peroxide solution ($H_2O_2$) is used as the etching agent. Further, when conductive polycrystalline silicon is used as the sacrificial layer 70, and SiN is used as the lower insulating layer 13 and the upper insulating layer 15, xenon difluoride gas ($XeF_2$) is used as the etching agent.

Note that the cavity 14 is not limited to being in a columnar shape, but may be in a polygonal column shape or the like. When the cavity 14 is in a polygonal column shape, the shapes in plain view of the upper electrode section 16A and the lower electrode section 12A are also preferably formed into polygonal shapes.

<Step S17> Formation of the Upper Electrode Layer

Figure 7E:
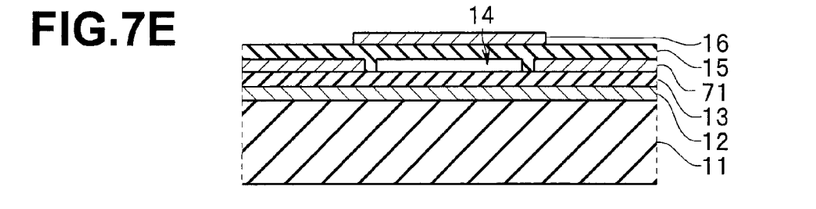
FIG. 7E is a sectional view for explaining the manufacturing method of the ultrasound cell of the first embodiment.

As shown in FIG. 7E, by the method and the material similar to those for the lower electrode layer 12, the upper electrode layer 16 that has the upper electrode section 16A and the upper wiring section 16B is formed.

<Step S18> Formation of the Protection Layer

Figure 7F:
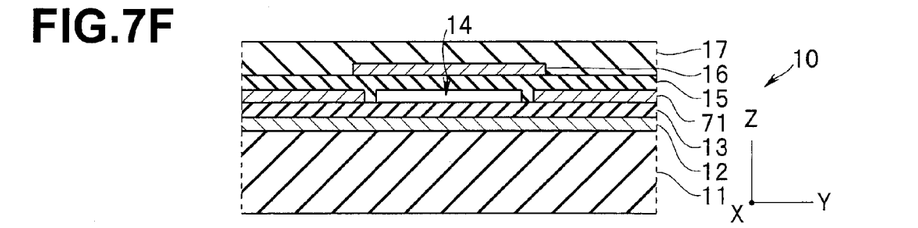
FIG. 7F is a sectional view for explaining the manufacturing method of the ultrasound cell of the first embodiment.

As shown in FIG. 7F, the surface of the US element 20 is covered with the protection layer 17. The protection layer 17 has not only a protection function, but also a sound matching layer function, and a function of connecting the US element 20.

Note that though explanation is omitted, the lower electrode terminal 52 is also formed in the lower electrode forming step, the upper electrode terminal 51 is also formed in the upper electrode forming step, and the shield electrode terminal 53 is also formed in the shield electrode forming step (sacrificial layer formation). The protection layer 17 is formed so as not to cover the lower electrode terminal 52, the upper electrode terminal 51 and the shield electrode terminal 53.

The protection layer 17 is formed of a flexible resin such as polyimide, epoxy, acryl or poly-para-xylene, and is especially preferably formed of polyimide, because polyimide has high chemical resistance, has a curving property, and is easy to process. Note that the protection layer 17 may have a two-layer structure in which a second insulating layer having biocompatibility is further formed on a first insulating layer.

Note that a plurality of ultrasound elements 20 are roundly disposed in a radial shape with a predetermined diameter in a connecting direction, whereby the US array 40 is produced. For example, the US array 40 is joined to an outer periphery of a cylinder with a predetermined diameter, for example. Further, the coaxial cable bundle 35 is connected to the US array 40, and the US unit 30 is produced.

<Action of US Element>

Next, with use of FIG. 10, an action of the US element 20 will be described. The lower electrode section 12A is connected to the voltage signal generating section 3A of the ultrasound observation apparatus 3 via the lower electrode terminal 52. The shield electrode section 71 is at the ground potential via the shield electrode terminal 53. On the other hand, the upper electrode section 16A is connected to the capacitance signal detection section 3B via the upper electrode terminal 51 to be at the ground potential. The capacitance signal detection section 3B detects a capacitance signal (current change).

At a time of generation of ultrasound, the voltage signal generating section 3A applies a drive voltage signal including a bias voltage to the lower electrode section 12A. When the voltage is applied to the lower electrode section 12A, the upper electrode section 16A at the ground potential is drawn to the lower electrode section 12A by an electrostatic force, and therefore, the membrane 18 that includes the upper electrode section 16A deforms. Subsequently, when voltage application to the lower electrode section 12A is eliminated, the membrane 18 is restored to an original shape by an elastic force. By deformation/restoration of the membrane 18, ultrasound is generated.

On the other hand, at the time of reception of ultrasound, the membrane 18 including the upper electrode section 16A is deformed by the received ultrasound energy. Thereupon, a distance between the upper electrode section 16A and the lower electrode section 12A changes, and therefore, the electrostatic capacitance therebetween also changes. Then, a current accompanying the capacitance change flows to the capacitance signal detection section 3B. Namely, the received ultrasound energy is converted into a capacitance signal.

Figure 10:
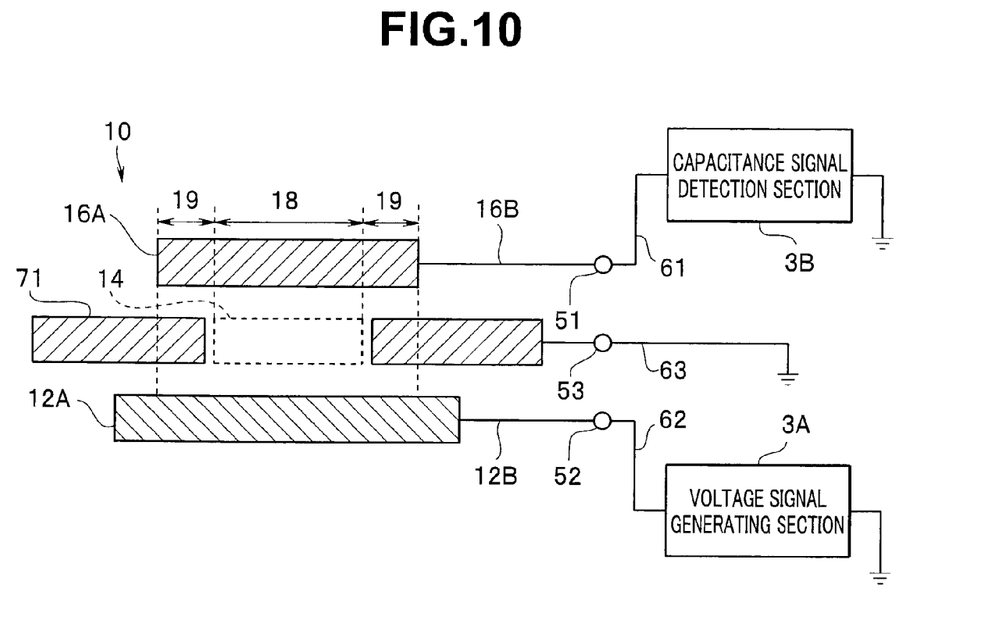
FIG. 10 is a schematic view for explaining an action of the ultrasound cell of the first embodiment.

Note that as shown in FIG. 6 and FIG. 10, in the US cell 10, a diameter R12 of the lower electrode section 12A that is substantially circular in plain view is larger than a diameter R16 of the upper electrode section 16A that is substantially circular in plain view, and further, the diameter R16 of the upper electrode section 16A that is substantially circular in plain view is larger than a diameter R14 of the cavity 14 that is substantially circular in plain view. Note that a straight line that connects centers of the lower electrode section 12A, the cavity 14 and the upper electrode section 16A is perpendicular to the silicon substrate 11.

Therefore, in the US cell 10, tolerance of pattern alignment precision of the respective layers that are formed by being stacked at the time of manufacture is large, and manufacture thereof is easy. In other words, even if pattern misalignment is large, the characteristics of the US cell 10 are stable.

However, for this reason, there is a part where the lower electrode section 12A and the upper electrode section 16A are disposed to face each other, in an outer circumferential region of the membrane 18. The facing portion forms a capacitor, and is a parasitic capacitance section (fixed capacitance section) 19 in which an electrostatic capacitance does not change even when ultrasound is received. When the electrostatic capacitance of the parasitic capacitance section 19 is large, even if the electrostatic capacitance of the membrane 18 (variable capacitance section) changes, a change rate of the capacitance signal (electrostatic capacitance) that is detected in the capacitance signal detection section 3B becomes small.

However, in the US element 20, the shield electrode section 71 at the ground potential is placed on the outer circumferential portion where the lower electrode section 12A and the upper electrode section 16A are disposed to face each other. Therefore, the upper electrode section 16A on the part where the lower electrode section 12A and the shield electrode section 71 are disposed to face each other does not form a capacitor with the lower electrode section 12A. Namely, the outer circumferential portion of the upper electrode section 16A does not become a cause of a parasitic capacitance. Therefore, the US element 20 has higher reception sensitivity of ultrasound than that of the US element that does not have the shield electrode section 71.

Further, as shown in FIG. 6 and the like, the lower wiring section 12B and the upper wiring section 16B in longitudinal directions thereof of the US element 20 are orthogonal to each other. Namely, the lower wiring section 12B is provided extensively in a Y axis direction from the lower electrode section 12A, whereas the upper wiring section 16B is provided extensively in an X axis direction from the upper electrode section 16A. In the US element 20 that does not have a region where the lower wiring section 12B and the upper wiring section 16B face each other, a parasitic capacitance does not occur between the lower wiring section 12B and the upper wiring section 16B, and therefore, reception sensitivity of ultrasound is high.

Second Embodiment

Next, a US element 20A and an ultrasound endoscope 2A that includes the US element 20A of a second embodiment will be described. Since the US element 20A and the US endoscope 2A are analogous to the US element 20 and the US endoscope 2, the same components are assigned with the same reference signs, and explanation thereof will be omitted.

Figure 11:
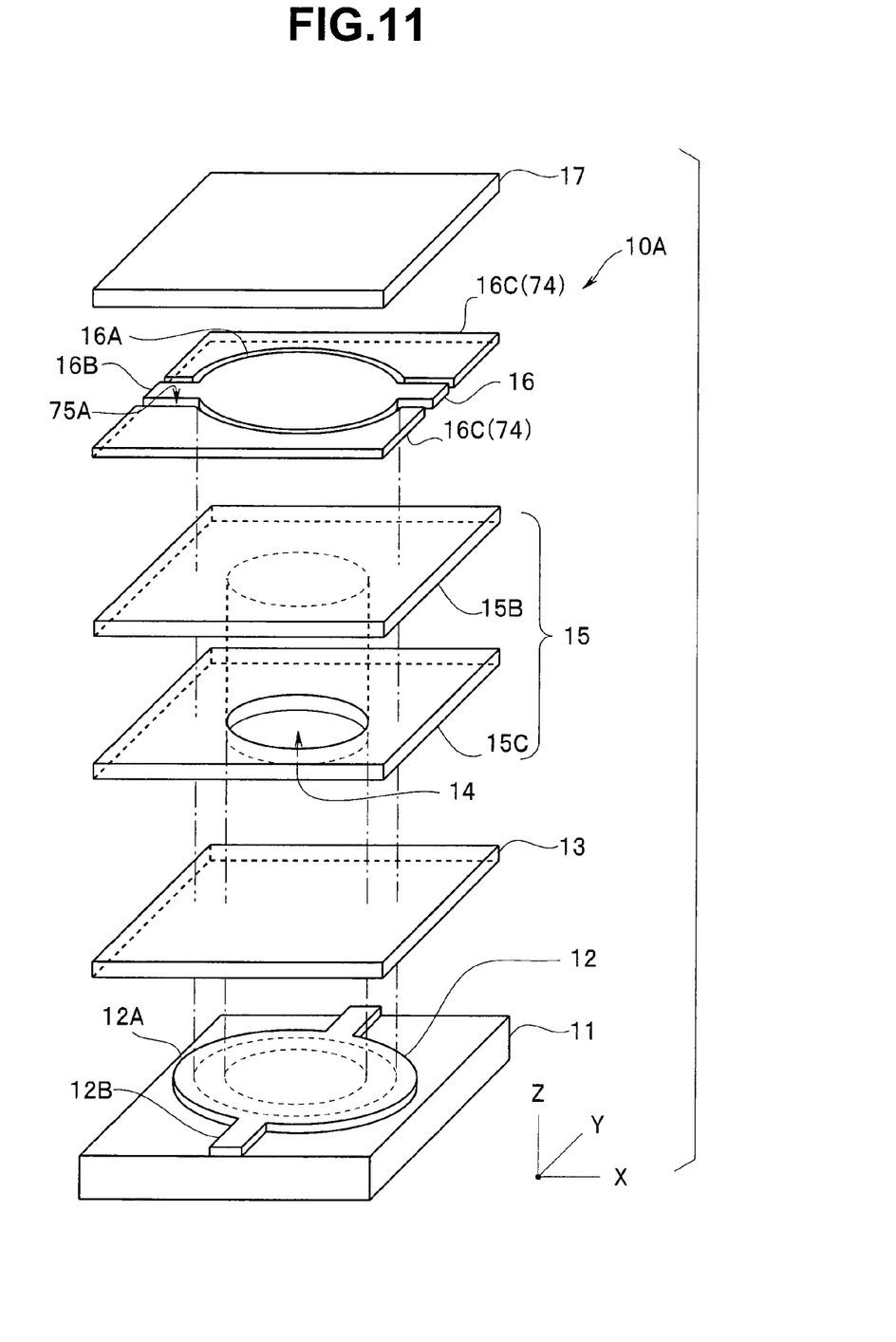
FIG. 11 is an exploded view for explaining a structure of an ultrasound cell of a second embodiment.

As shown in FIG. 11, in the US element 20A, a part (16C) of a layer formed of a conductive material deposited to form the upper electrode layer 16 is a shield electrode section 74. Namely, the shield electrode section 74 is a region that is formed of the same material as the upper electrode layer 16 simultaneously with the upper electrode layer 16, and is separated from the upper electrode layer 16 by a groove section 75A.

Figure 12:
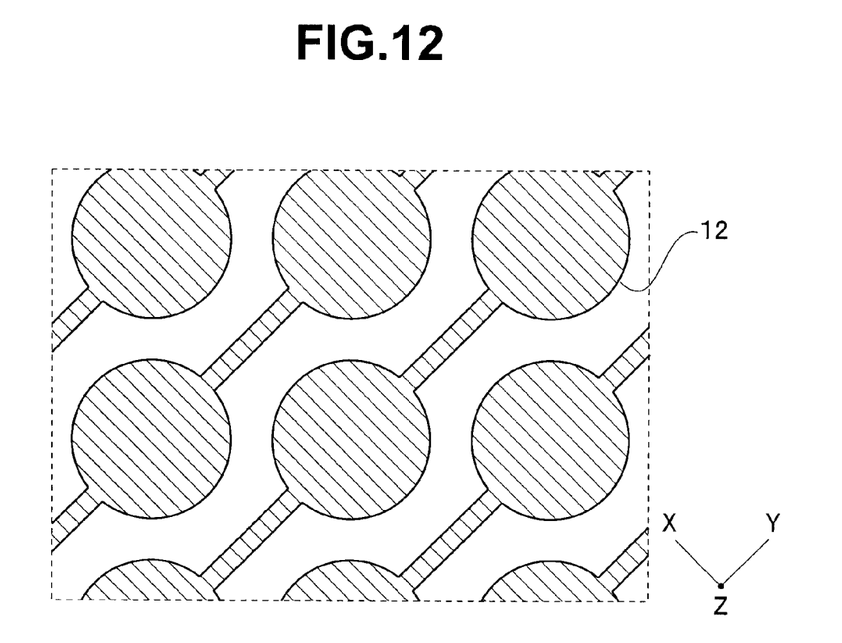
FIG. 12 is a top view showing a pattern of a lower electrode layer of the ultrasound cell of the second embodiment.
Figure 13:
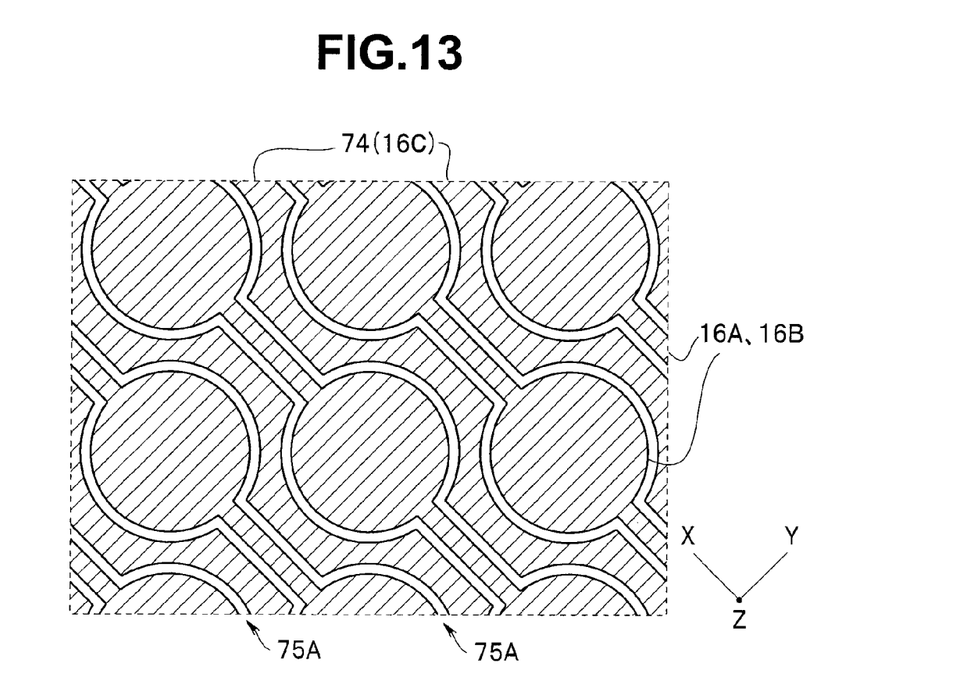
FIG. 13 is a top view showing a pattern of an upper electrode layer of the ultrasound cell of the second embodiment.

Here, FIG. 12 shows a pattern of the lower electrode layer 12. As is already described, the lower electrode layer 12 is worked to have a pattern that is formed by the lower electrode section 12A and the lower wiring section 12B by an etching process being performed via a mask, after a conductive material layer is formed on an entire surface.

In contrast with the above, as shown in FIG. 12, the upper electrode layer 16 is separated from the shield electrode section 74 by the groove section 75A by an etching process being performed via a mask after a conductive material layer is formed on an entire surface.

In the US element 20A that includes the shield electrode section 74, even if a part of the insulating film is broken due to dust, a defect or the like, voltage signals (a drive signal and a bias signal) that are applied to the lower electrode layer 12 do not leak to an outside of the US element 20A. Therefore, characteristics of the US element 20A and the US endoscope 2A are stable.

Further, since the shield electrode section 74 is produced simultaneously with the upper electrode layer 16, increase in the number of steps is small, and manufacture thereof is easy.

Third Embodiment

Next, a US element 20B and an ultrasound endoscope 2B including the US element 20B of a third embodiment will be described. Since the US element 20B and the US endoscope 2B are analogous to the US elements 20 and 20A and the US endoscopes 2 and 2A, the same components will be assigned with the same reference signs, and explanation thereof will be omitted.

Figure 14:
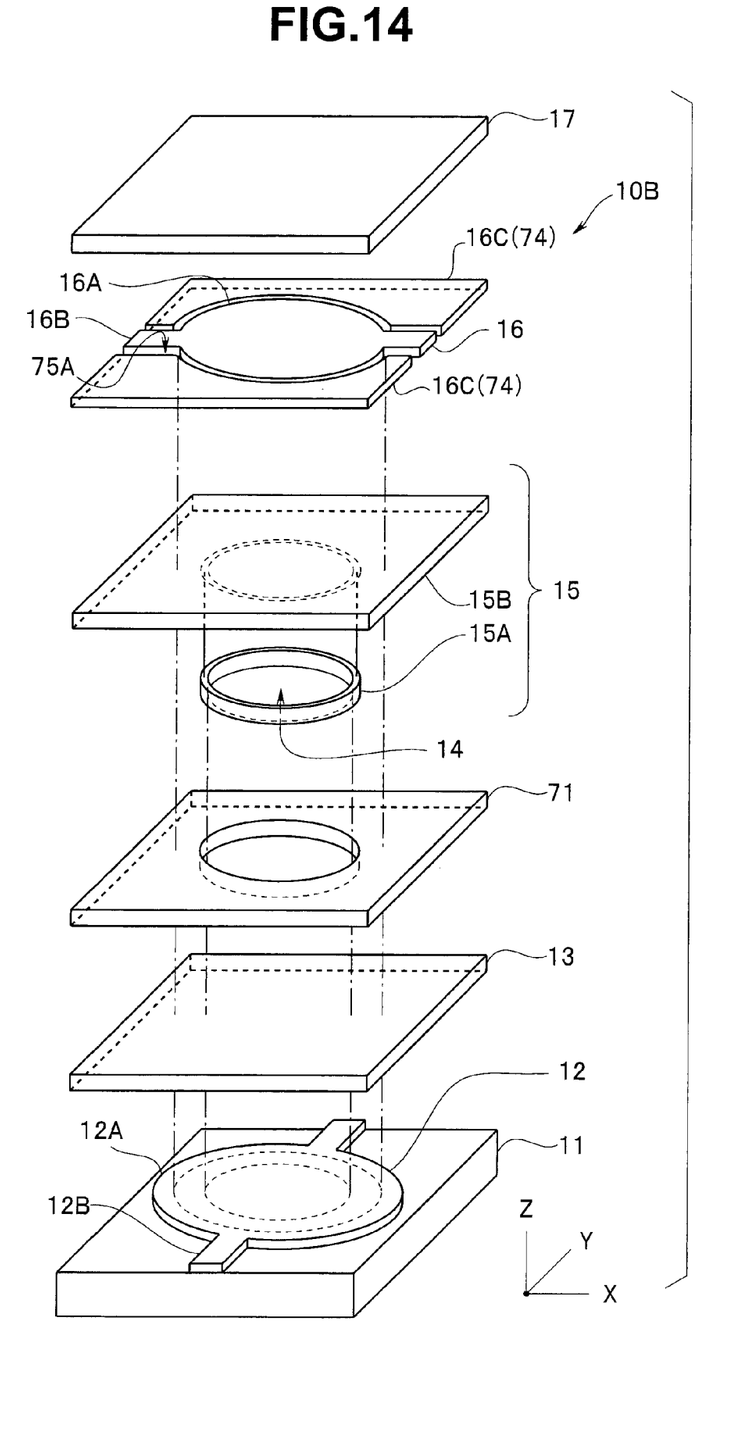
FIG. 14 is an exploded view for explaining a structure of an ultrasound cell of a third embodiment.

As shown in FIG. 14, in a US element 20B, a shield electrode section includes a first shield electrode section 71 and a second shield electrode section 73. The first shield electrode section 71 is formed by a remaining region of the sacrificial layer 70 that is not removed by an etching process similarly to the one that is included by the US element 20. The second shield electrode section 73 is a region that is formed simultaneously with the upper electrode layer 16 similarly to the one that is included by the US element 20A, and is separated from the upper electrode layer 16 by the groove section 75A.

The US element 20B and the US endoscope 2B include the two shield electrode sections 71 and 73, and therefore, have more stable characteristics than the US elements 20 and 10A and the US endoscopes 2 and 2A.

Fourth Embodiment

Next, a US element 20C and an ultrasound endoscope 2C that includes the US element 20C of a fourth embodiment will be described. Since the US element 20C and the US endoscope 2C are analogous to the US element 20 and the US endoscope 2, the same components are assigned with the same reference signs, and explanation thereof will be omitted.

Figure 15:
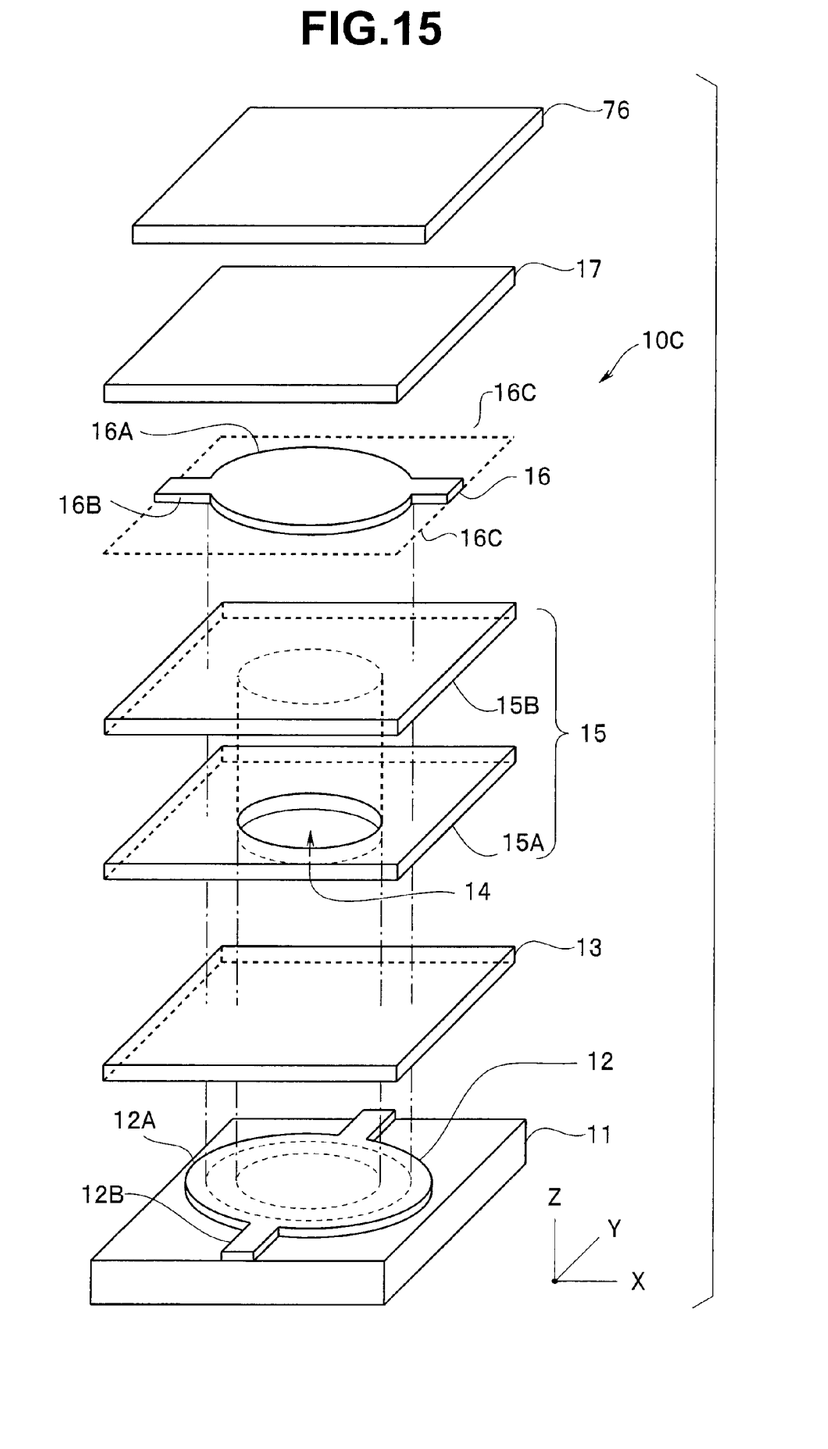
FIG. 15 is an exploded view for explaining a structure of an ultrasound cell of a fourth embodiment.

As shown in FIG. 15, in the US element 20C, the entire surface at an upper side of the lower electrode layer 12 is covered with a shield electrode section 76 via the protection layer 17. The shield electrode section 76 is formed from a conductive material, for example, aluminum, titanium, a conductive plastic or the like. Note that the shield electrode section 76 may be further covered with a second protection layer (not illustrated). In other words, the shield electrode section 76 may be made an intermediate layer of the protection layers of a multilayer structure.

The US element 20C has a problem that the membrane 18 is thick by the amount of the shield electrode section 76, and therefore, becomes difficult to vibrate. Further, it is necessary to add a step of forming the shield electrode section 76.

However, even if a part of the insulating film is broken due to dust, a defect or the like in the US element 20C, the voltage signals (the drive signal and the bias signal) that are applied to the lower electrode layer 12 do not leak to the outside of the US element 20C. Therefore, the characteristics of the US element 20C and the US endoscope 2C are stable.

The present invention is not limited to the embodiments described above, and various modifications, alterations and the like can be made within the range without changing the gist of the present invention.

What is claimed is:

1. An ultrasound element, comprising a base substrate,
   wherein a lower electrode layer that has a plurality of lower electrode sections, and a plurality of lower wiring sections that connect the plurality of lower electrode sections, and is connected to a lower electrode terminal to which a drive signal and a bias signal are applied,
   a lower insulating layer,
   an upper insulating layer in which a plurality of cavities are formed,
   an upper electrode layer that has a plurality of upper electrode sections that are disposed to face the respective lower electrode sections via the respective cavities, and a plurality of upper wiring sections that connect the plurality of upper electrode sections, and is connected to an upper electrode terminal at a ground potential, for detecting a capacitance signal, and
   a protection layer are sequentially stacked on the base substrate,
   the ultrasound element further comprising:
   a first shield electrode section that is formed at least at an upper side of the lower wiring sections and at a lower side of the upper electrode sections, in a region including regions where the upper electrode sections and the lower electrode sections are disposed to face each other, the first shield electrode section being connected to a shield electrode terminal at a ground potential.

2. The ultrasound element according to claim 1,
   wherein the cavities are regions where a sacrificial layer that is covered with the upper insulating layer and is formed of a conductive material is partially removed by an etching process, and
   the first shield electrode section is a remaining region of the sacrificial layer that is not removed by the etching process.

3. The ultrasound element according to claim 1,
   further comprising a second shield electrode section,
   wherein the cavities are regions where a sacrificial layer that is covered with the upper insulating layer and is formed of a conductive material is partially removed by an etching process, and
   the first shield electrode section is a remaining region of the sacrificial layer that is not removed by the etching process, and the second shield electrode section is a region that is formed simultaneously with the upper electrode layer, and is separated from the upper electrode layer by a groove section.

4. The ultrasound element according to claim 1, wherein the first shield electrode section covers an entire surface of an upper side of the lower electrode layer via the protection layer.

5. An ultrasound endoscope, comprising a base substrate,
   wherein a lower electrode layer that has a plurality of lower electrode sections, and a plurality of lower wiring sections that connect the plurality of lower electrode sections, and is connected to a lower electrode terminal to which a drive signal and a bias signal are applied, a lower insulating layer, an upper insulating layer in which a plurality of cavities are formed, an upper electrode layer that has a plurality of upper electrode sections that are disposed to face the respective lower electrode sections via the respective cavities, and a plurality of upper wiring sections that connect the plurality of upper electrode sections, and is connected to an upper electrode terminal at a ground potential, for detecting a capacitance signal, and a protection layer are sequentially stacked on the base substrate, the ultrasound element further comprising:

a first shield electrode section that is formed at least at an upper side of the lower wiring sections and at a lower side of the upper electrode sections, in a region including regions where the upper electrode sections and the lower electrode sections are disposed to face each other, the first shield electrode section being connected to a shield electrode terminal at a ground potential.

6. The ultrasound endoscope according to claim 5, wherein the cavities are regions where a sacrificial layer that is covered with the upper insulating layer and is formed of a conductive material is partially removed by an etching process, and the first shield electrode section is a remaining region of the sacrificial layer that is not removed by the etching process.

7. The ultrasound endoscope according to claim 5, further comprising a first shield electrode section and a second shield electrode section, wherein the cavities are regions where a sacrificial layer that is covered with the upper insulating layer and is formed of a conductive material is partially removed by an etching process, and the first shield electrode section is a remaining region of the sacrificial layer that is not removed by the etching process, and the second shield electrode section is a region that is formed simultaneously with the upper electrode layer, and is separated from the upper electrode layer by a groove section.

8. The ultrasound endoscope according to claim 5, wherein the first shield electrode section covers an entire surface of an upper side of the lower electrode layer via the protection layer.

* * * * *